(12) United States Patent
Kapel et al.

(10) Patent No.: US 11,110,133 B2
(45) Date of Patent: Sep. 7, 2021

(54) LYOPHILIZED COMPOSITION FOR PRESERVING MICROBIOTA IN ITS ECOSYSTEM

(71) Applicants: INSTITUT NATIONAL DE LA RECHERCHE AGRONOMIQUE, Paris (FR); UNIVERSITE PARIS DESCARTES, Paris (FR); UNIVERSITE PARIS DIDEROT—PARIS 7, Paris (FR); ASSISTANCE PUBLIQUE—HOPITAUX DE PARIS, Paris (FR)

(72) Inventors: Nathalie Kapel, Paris (FR); Anne-Judith Waligora-Dupriet, Clamart (FR); Muriel Thomas, Igny (FR); Christine Charrueau, Athis-Mons (FR); Francisca Joly, Paris (FR); Camille Mayeur, Fontenay-le-Fleury (FR); Véronique Robert, Limours-en-Hurepoix (FR); Johanne Delannoy, Cergy-le-Haut (FR)

(73) Assignees: INSTITUT NATIONAL DE RECHERCHE POUR L'AGRICULTURE, L'ALIMENTATION ET L'ENVIRONNEMENT, Paris (FR); UNIVERSITE PARIS DESCARTES, Paris (FR); UNIVERSITE PARIS DIDEROT—PARIS 7, Paris (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 0 days.

(21) Appl. No.: 16/062,302

(22) PCT Filed: Dec. 16, 2016

(86) PCT No.: PCT/EP2016/081603
§ 371 (c)(1),
(2) Date: Jun. 14, 2018

(87) PCT Pub. No.: WO2017/103225
PCT Pub. Date: Jun. 22, 2017

(65) Prior Publication Data
US 2019/0134110 A1    May 9, 2019

(30) Foreign Application Priority Data
Dec. 18, 2015 (FR) .................................... 1562836

(51) Int. Cl.
*A61K 35/741* (2015.01)
*A61K 9/16* (2006.01)
*A61K 9/19* (2006.01)
*C12N 1/04* (2006.01)

(52) U.S. Cl.
CPC .......... *A61K 35/741* (2013.01); *A61K 9/1652* (2013.01); *A61K 9/19* (2013.01); *C12N 1/04* (2013.01)

(58) Field of Classification Search
CPC ...... A61K 35/741; A61K 9/18; A61K 9/1652; C12N 1/04
See application file for complete search history.

(56) References Cited

U.S. PATENT DOCUMENTS

2018/0099012 A1    4/2018 Affagard et al.

FOREIGN PATENT DOCUMENTS

| WO | 2007070052 A2 | 6/2007 |
|----|---------------|--------|
| WO | 2008035332 A1 | 3/2008 |
| WO | 2012016287 A2 | 2/2012 |
| WO | 2013142792 A1 | 9/2013 |
| WO | 2014152484 A1 | 9/2014 |
| WO | 2016170285 A1 | 10/2016 |

OTHER PUBLICATIONS

U.S. Appl. No. 16/063,419 (Year: 2015).*
Written Opinion of the International Searching Authority dated Feb. 1, 2017, issued in corresponding International Application No. PCT/EP2016/081603, filed Dec. 16, 2016, 10 pages.
International Preliminary Report on Patentability dated Jun. 19, 2018, issued in corresponding International Application No. PCT/EP2016/081603, filed Dec. 16, 2016, 1 page.
International Search Report dated Feb. 1, 2017, issued in corresponding International Application No. PCT/EP2016/081603, filed Dec. 16, 2016, 5 pages.
Borody, T.J., et al., "Fecal Microbiota Transplantation: Expanding Horizons for Clostridium difficile Infections and Beyond", Antibiotics 4(3):254-266, Jul. 6, 2015.
Lin, E., et al., "Twelve Week Storage Trial of Microbial Viability in Lyophilized and Frozen Fecal Microbiota Preparations," Gastroenterology 148(4) Supplement 1, p. S-962, Apr. 2015.
Semyonov, D., et al., "Microencapsulation of Lactobacillus paracasei by spray freeze drying," Food Research International 43(1):193-202, Jan. 1, 2010.
Tian, H., et al., "Freeze-dried, Capsulized Fecal Microbiota Transplantation for Relapsing Clostridium difficile Infection," Journal of Clinical Gastroenterology 49(6), Jul. 2015, 4 pages.
Youngster, I., et al., "Oral, capsulized, frozen fecal microbiota transplantation for relapsing Clostridium difficile infection," The Journal of the American Medical Association 312(17):1772-1778, Oct. 11, 2014.

* cited by examiner

*Primary Examiner* — Ruth A Davis
(74) *Attorney, Agent, or Firm* — Christensen O'Connor Johnson Kindness PLLC (57) ABSTRACT

The invention relates to a lyophilized composition comprising a microbiota in its ecosystem, in particular stools, and a mixture of cryoprotectant agents comprising maltodextrin and trehalose, a capsule comprising said lyophilized composition, the use thereof, and methods for the production thereof.

11 Claims, 6 Drawing Sheets

LYOPHILIZED COMPOSITION FOR PRESERVING MICROBIOTA IN ITS ECOSYSTEM

This invention relates to the field of preservation of a microbiota in its ecosystem (MIIE) in the form of a lyophilizate. More particularly, it relates to a lyophilized stool composition whereby faecal microbiota can be preserved for up to several months for the purpose of human transplantation. The invention also relates to the therapeutic use in humans or animals of said composition, particularly in the form of capsules for oral administration.

Many studies have demonstrated the importance of faecal microbiota transplantation (FMT) for the therapeutic management of certain pathologies that involve an imbalance of the faecal microbiota in its ecosystem, called dysbiosis, such as for example *Clostridium difficile* infections and their recurrence (Van Nood E. et al., 2013). FMT is already associated with a high level of clinical evidence and the implementation of this technique for this purpose is therefore mentioned in the latest European (Debast S B. et al., 2014) and North American (Surawicz C M. et al., 2013) recommendations. The implementation of this technique in other pathological contexts of dysbiosis, such as inflammatory bowel disease, irritable bowel syndrome, metabolic syndrome, obesity, diabetes, multidrug-resistant bacteria, or neurological developmental disorders, the causes of which are uncertain or unknown, is also envisaged (Vrieze A. et al., 2013, Kelly C R. et al., 2015).

Despite the enthusiasm in recent years shown by the medical community and emerging patient demand, there is currently no standardized procedure to conduct an FMT, nor is there a method for selecting the donor, for preparing the stools or for choosing the route of administration.

In general, the donor is selected on the basis of a clinical examination and after screening for a large range of pathogens, such as bacteria, viruses or parasites, conducted prior to the donation; this results in a validation rate of potential donors of less than 20% (Borody T. et al., 2015). This, in addition to delays in obtaining pathogen results, severely limits the number of usable donations.

The modalities governing the administration of an FMT are diverse. The faecal microbiota can be administered by nasogastric or nasoduodenal probe, in the course of a colonoscopy, or by rectal enema (Kelly C R. et al., 2015), each method having its own advantages and disadvantages. The nasogastric or nasoduodenal paths, for example, can be badly perceived by the person being treated, and can induce a risk of vomiting or ingestion that require x-ray monitoring during the insertion of the probe. The use of colic probes is interesting in that it allows for the observation of the mucosa during administration; however, it is also with significant morbidity factors and a high cost. Finally, the rectal enema method is easier to implement and less costly; however, it is difficult to ensure that the administered material is retained by the treated individual. These issues are compounded by reluctance on the part of patients relating to the organoleptic properties of the preparation.

The current recommendations from the "Groupe Français de Transplantation Fécale" (French Group for Faecal Transplantation) regarding *Clostridium difficile* colitis (Sokol H. et al., 2015) and by the ANSM for clinical trials (ANSM, 2015) relate to an administration occurring within 6 hours following the passing of stools. To facilitate access to the donation, preserved faecal preparations frozen at −80° C. and therefore readily available are proposed. Their efficacy is similar to that observed with transplants using fresh material (Hamilton M J. et al., 2012; Youngster I. et al., 2014a; Lee et al., 2016). These frozen preparations require dilution in a solution containing a cryoprotectant to protect the microbiota from the effects of freezing. The only cryoprotectant described in literature for freezing stools for the purpose of transplantation is glycerol at a concentration of 10%. The effectiveness of a transplant performed with frozen preparations containing glycerol is maintained for up to 5 months following their preparation (Younster I. et al., 2014a).

The oral administration of capsules filled with this material and stored at −80° C. was reported with satisfactory results (Youngster I. et al., 2014b; Younster et al., 2016). This type of preparation therefore opens new prospects for a galenic approach facilitating administration to the person under treatment, specifically the patient. However, it currently still involves a highly empirical production and requires preservation at −80° C., which gives rise to storage issues.

There is therefore an unmet need for stool preparations whereby their preparation and storage are facilitated while preserving the original qualities of the faecal microbiota during its storage period. Such stool preparations would have to be available in a galenic form that enables the initial administration of a small volume through a comfortable and non-invasive route of administration.

In this context, the inventors have developed a lyophilized stool composition diluted in an optimized mixture of cryoprotectants in order to facilitate the production, availability and long-term storage of faecal preparations, while improving the acceptability and comfort for the persons undergoing treatment.

Lyophilization is a preservation process used in the pharmaceutical industry for the preservation of bacterial strains. Lyophilization should be performed in optimal conditions to maintain the viability and equilibrium of different bacterial genera, particularly in the case of complex mixtures such as the MIIE in general and faeces in particular. The use of suitable cryoprotectants ensures full or at least partial survival of the bacteria when they are frozen.

There are three categories of cryoprotectant molecules for living organisms, in particular for bacteria:
- molecules with a high molecular weight and kept in an extracellular medium, such as proteins and polysaccharides, which facilitate the aqueous efflux from cells during the freezing phase, thereby limiting the formation of intracellular ice crystals. By increasing the viscosity of the extracellular medium, these molecules also reduce crystal growth;
- molecules that are capable of crossing cell walls, such as amino acids and oligosaccharides;
- molecules that penetrate cell walls and cytoplasmic membranes, such as DMSO and glycerol (Carvalho A. S. et al., 2004).

The penetrants agents of the second and third categories limit cellular dehydration and lower the freezing temperature inside the cell, thereby reducing the salt concentration and decreasing the osmotic shock (Béal C. et al., 2015).

Figure 2:
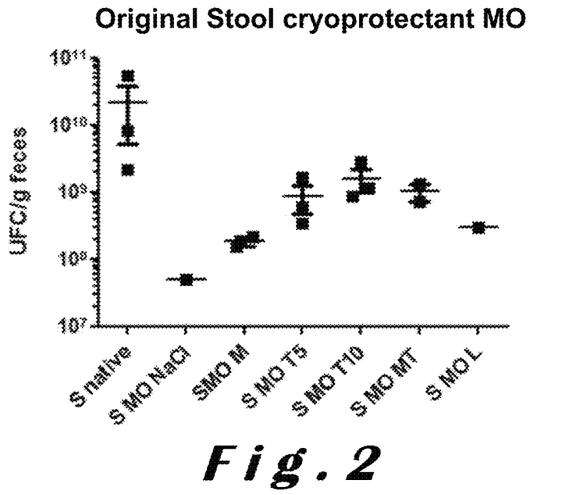
FIG. 2: Representation for the original stool of the viable bacterial load after reconstitution of the lyophilizate depending on the nature of the cryoprotectant: 5% maltodextrin (M), 5% trehalose (T5) 10% trehalose (T10), mixture of 6.7% maltodextrin and 10% trehalose (MT) or milk (L).
Figure 3:
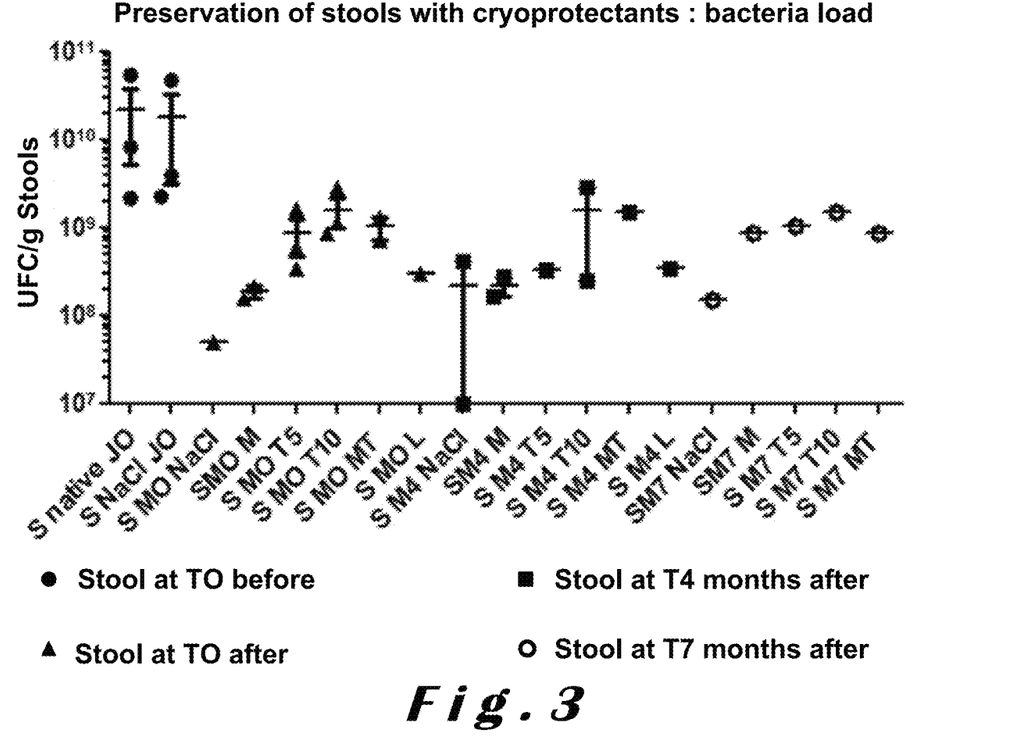
FIG. 3: Representation of the evolution of the bacterial load over time depending on the nature of the cryoprotectant: 5% trehalose (T5), 10% trehalose (T10) and mixture of 6.7% maltodextrin and 10% trehalose (MT). J0 represents pre-lyophilization; M0 is post-lyophilization; M4 is 4 months post-lyophilization and M7 is 7 months post-lyophilization.
Figure 4:
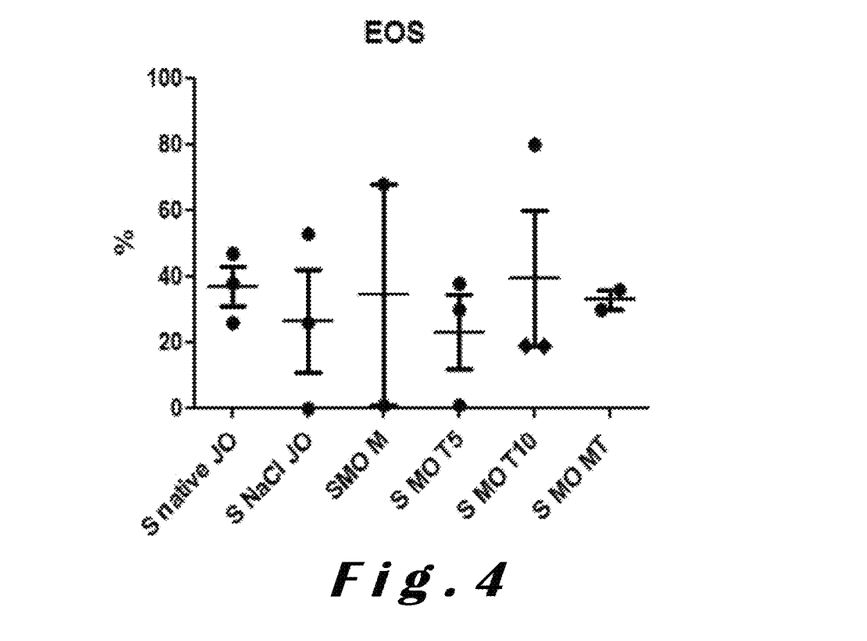
FIG. 4: Representation of the percentage of EOS bacteria at M0, depending on the nature of the cryoprotectant: maltodextrin 5% (M), trehalose 5% (T5), 10% trehalose (T10), mixture of 6.7% maltodextrin and 10% trehalose (MT). J0 represents pre-lyophilization; M0 is post-lyophilization.
Figure 5:
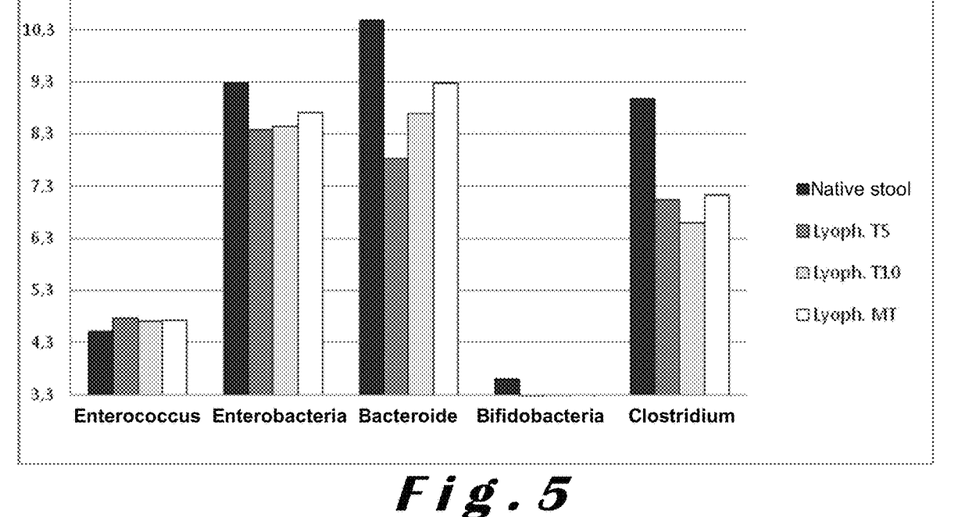
FIG. 5: Representation of the main bacterial groups found in the native stool and in the lyophilizates directly after their preparation, depending on the nature of the cryoprotectant: 5% trehalose (T5), 10% trehalose (T10) and mixture of 6.7% maltodextrin and 10% trehalose (MT). The results presented in FIG. 5 show those obtained for stool 3.
Figure 6:
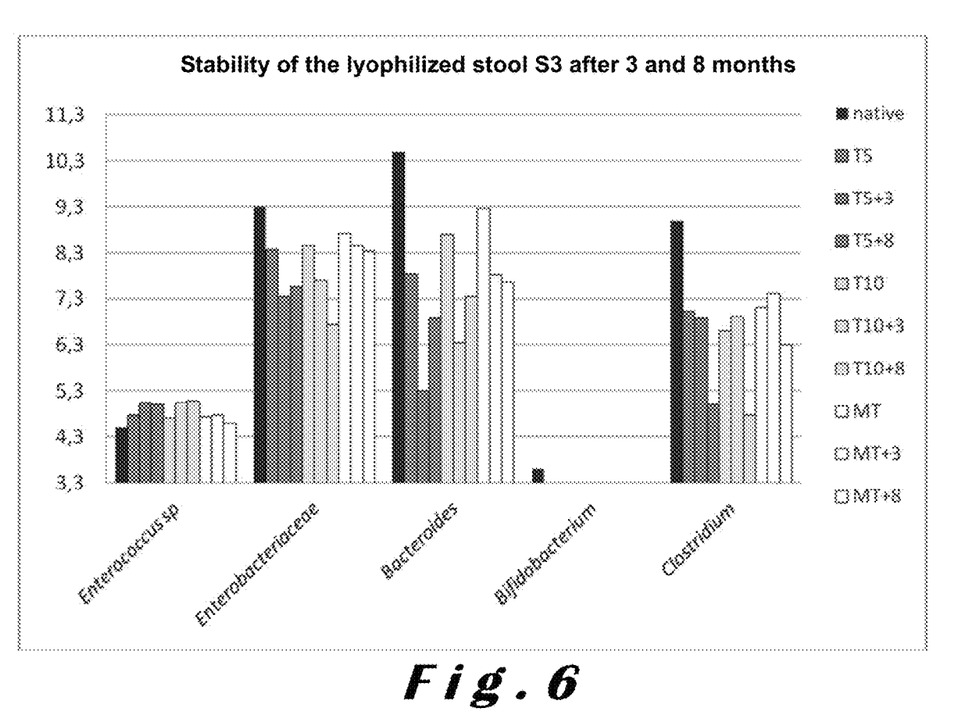
FIG. 6: Representation of the main bacterial groups found in the native stool and in the lyophilizates after their preparation (M0), depending on the nature of the cryoprotectant: 5% trehalose (T5), 10% trehalose (T10) and mixture of 6.7% maltodextrin and 10% trehalose (MT). The results are presented immediately after lyophilization and after storage at 4° C. for 3 months (+3) and 8 months (+8). The results presented in FIG. 6 show those obtained for stool 3.
Figure 7:
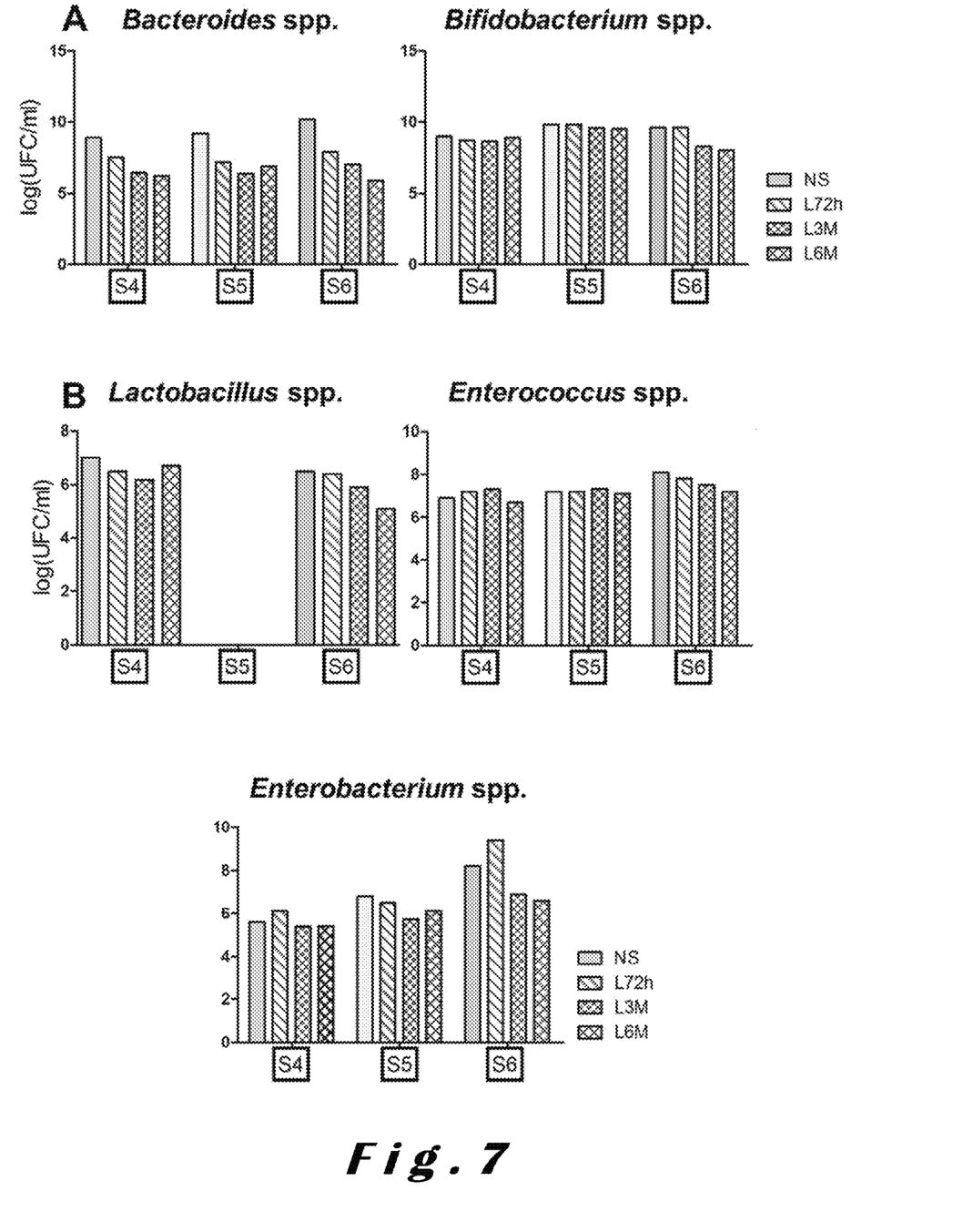
FIG. 7: Representation of the impact of lyophilization (L72h) and the preservation of lyophilizates for 3 months (L3M) and 6 months (L6M) on the viability of the main bacterial groups in three stool samples (S4, S5, S6) compared with the native stool (NS). (A) Effect of different strictly anaerobic bacterial populations. (B) Effect on different optionally aerobic/anaerobic bacterial populations.
Figure 8:
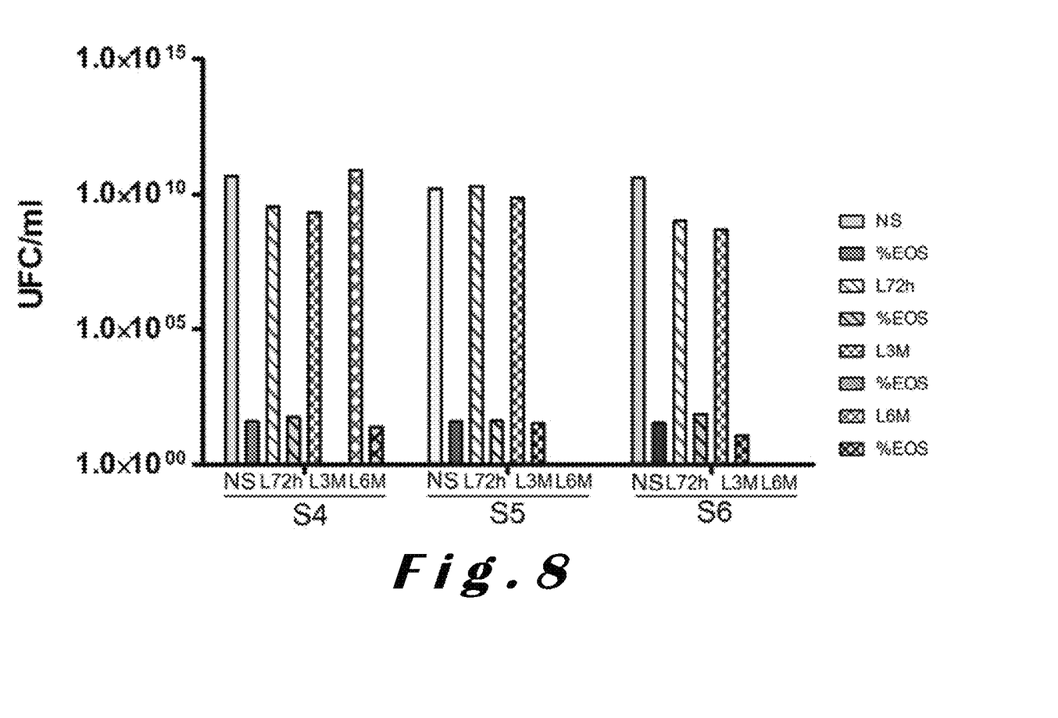
FIG. 8: Representation of the impact of lyophilization (L72h) and the preservation of lyophilizates for 3 months (L3M) and 6 months (L6M) on the viability of bacteria extremely oxygen sensitive (EOS) in various stool samples (S4, S5, S6) compared with the native stool (NS).
Figure 9:
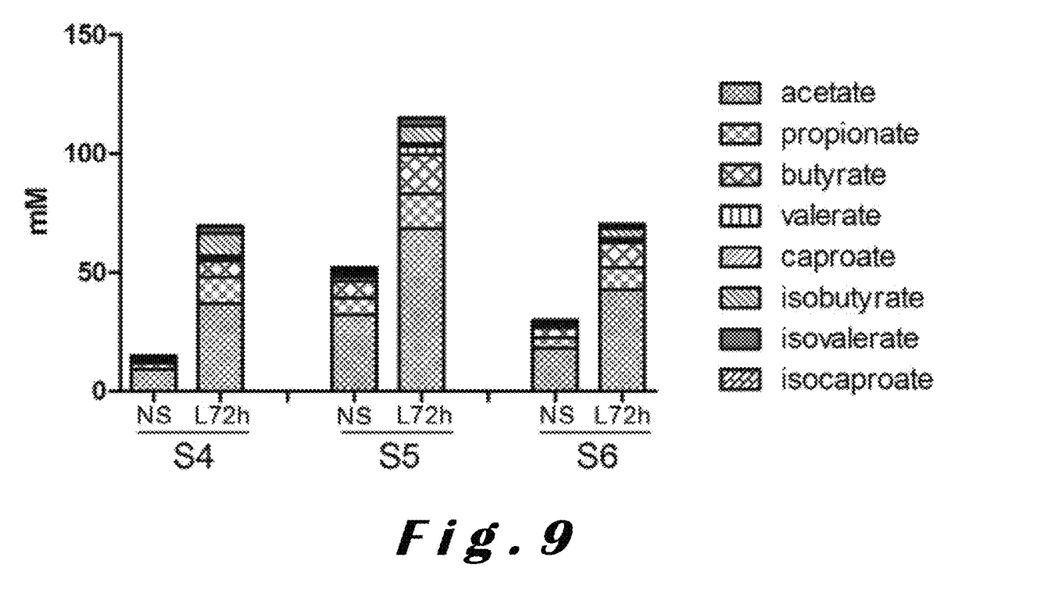
FIG. 9: Assessment of the evolution of bacterial metabolites by gas chromatography conducted on native stools (NS) and lyophilized stools (L72H).
Figure 10:
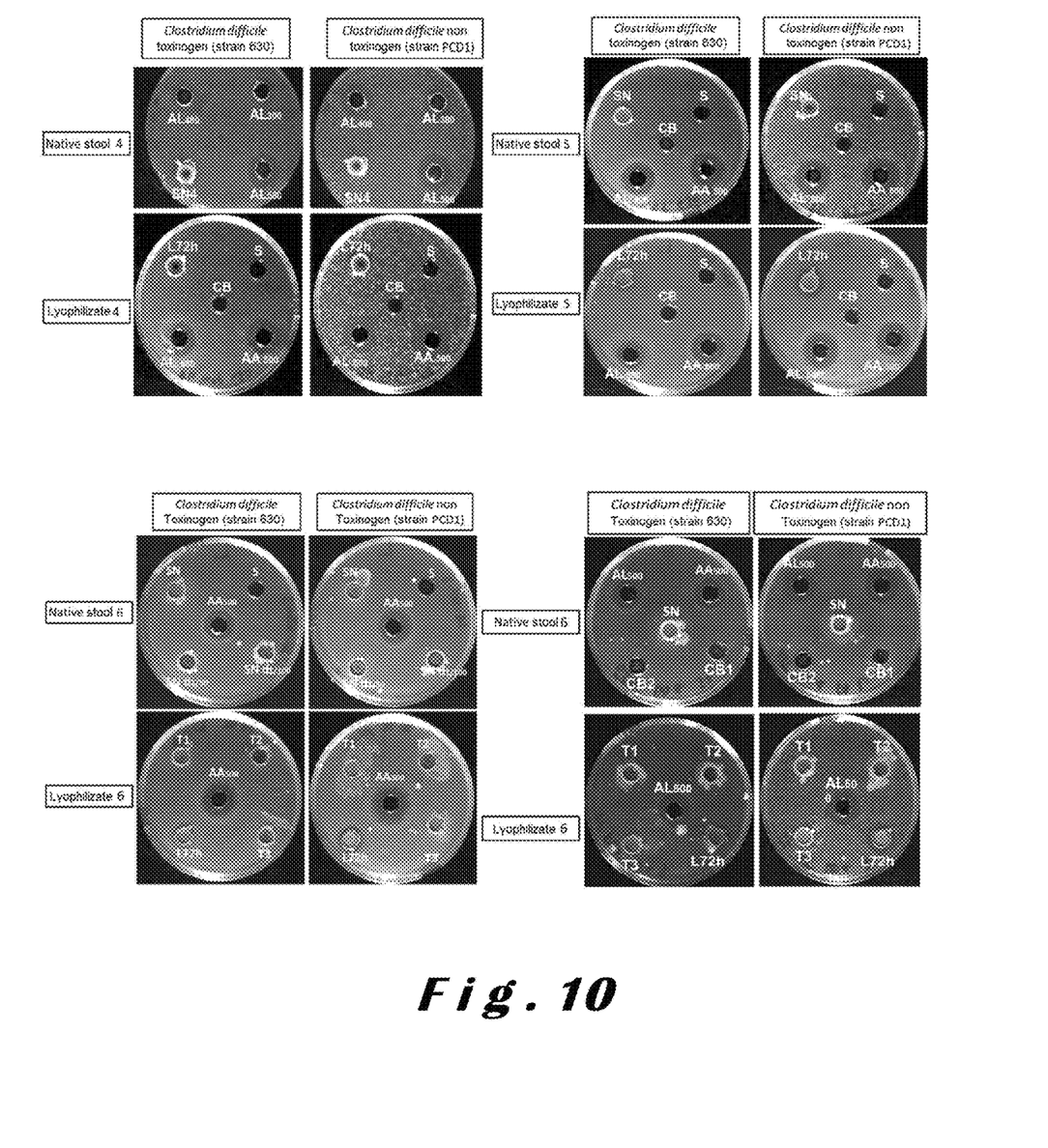
FIG. 10: Assessment of the anti-*Clostridium difficile* effect of native (S or NS) and lyophilized stools (L72h).

To optimize the preservation of the living organisms of faecal microbiota, the inventors assessed several cryoprotectants, used individually or in combination. Glycerol at 10%, generally used for FMT conducted with frozen material (Hamilton M J. et al, 2012; Youngster I. et al., 2014a) does not seem suited to the production of a lyophilizate. Among tested cryoprotectants, two have shown some promise: maltodextrin and trehalose. Although trehalose yields good results, the results achieved with a mixture of maltodextrin and trehalose are further improved, both in terms of maintaining the viability of the microbiota (FIGS. 1 and 2) and in terms of maintaining its diversity (FIG. 5). Maintaining diversity is particularly important as the purpose of the FMT is precisely to restore the balance between the different populations in the intestinal ecosystem of the recipient. The protective effects of a mixture of maltodextrin and trehalose for the microbiota are observed for at least 3 months after lyophilization, and even for up to 7 months thereafter (FIGS. 3, 6 and 7). Furthermore, the mixture of maltodextrin and trehalose is more favourable for maintaining the viability of bacteria that show extreme oxygen sensitivity (EOS), such as bacteria of the *Clostridium leptum* group (FIGS. 4 and 8). In addition, the concentration of bacterial metabolites such as short-chain fatty acids that are representative of the functional capabilities of the faecal microbiota is maintained and even increased in the lyophilizate when compared with the native stool (FIG. 9). Finally, anti-*Clostridium difficile* activity of the lyophilizate is demonstrated in vitro with inhibited bacterial growth for 2 strains *Clostridium difficile*, one of which is toxinogen (strain 630) and the other is non-toxinogen (PCD1 strain) (FIG. 10).

Therefore, the invention relates to the use of a mixture of cryoprotectants for preservation a microbiota in its ecosystem (MIIE) in a lyophilized form, characterized in that said mixture of cryoprotectants comprises maltodextrin (M) and trehalose (T) in a M/T weight ratio ranging between 35/65 and 45/55.

Maltodextrin is a polysaccharide cryoprotectant that doesn't penetrate cell walls, whereas trehalose is an oligosaccharide cryoprotectant that penetrates cell walls.

The term "microbiota in its ecosystem" or MIIE describes a microbiota whose composition is unchanged compared with the microbiota existing naturally in the body. Microbiota and its ecosystem constitute a complex and rich mixture, made up largely of bacteria, fungi, viruses, and bacteriophages, but also cell debris, many peptides and proteins secreted by enterocytes and lamina propria cells with their excretion/secretion products, such as secretory IgA, calprotectin, cytokines and other anti-inflammatory or antimicrobial peptides of the defensin type, bacterial products secreted or not, including metabolites such as short-chain fatty acids, bacteriocins, and any other biologically active molecules produced by bacteria or other microorganisms of the microbiota, mucus, monosaccharide and polysaccharide-type carbohydrate compounds, and trace elements. The MIIE is therefore a complex matrix that can be described as living, and in which many molecular and cellular interactions occur.

The MIIE may be stored in lyophilized form by using a mixture of maltodextrin and trehalose according to the invention. As examples, the MIIE that can be preserved by this method are the intestinal microbiota, formerly known as intestinal flora, the faecal microbiota contained in stools, and vaginal microbiota formerly called vaginal flora. Each of these examples of microbiota is characterised by dominant bacterial groups that are well known to the person skilled in the art.

In a preferred embodiment, the MIIE to preserve consists of stools.

According to the invention, the term "lyophilization" describes the process of removing water from a product by freezing the product and then by evaporating the ice in a vacuum without passing through the liquid state, which is a phenomenon called sublimation. This technique is well known to the person skilled in the art. There are three major phases in a lyophilization cycle:

freezing, where the products are refrigerated at temperatures of −20° C. to −80° C.; water is transformed into ice;

primary drying in a vacuum, which is the phase where interstitial free ice undergoes sublimation;

final drying, whereby the water molecules trapped at the surface of dried products are extracted by desorption.

In this invention, the term "stool" is used to describe faecal matter obtained following the absorption of food, its digestion, and its transit through the intestinal tract. Stools normally consist of water at 75-85% of their weight, and of dry matter at 15-25% of their weight [desquamated intestinal cells and immune cells from the lamina propria with their excretion/secretion products, such as secretory IgA, calprotectin, cytokines and other anti-inflammatory or antimicrobial peptides . . . , constituting elements of the microbiota (bacteria, viruses, fungi, bacteriophages) and bacterial products secreted or not, including metabolites such as short-chain fatty acids, bacteriocins, and any other biologically active molecules produced by bacteria or other microorganisms of the microbiota; mucus; cellular debris including fibres and cellulose coming from the indigestible portion of plants, lipids, iron, trace elements . . . ]. According to the invention, the term stool describes recently-passed stools by a healthy individual. The selection of donors among humans and the stool preparation can be conducted according to the protocol and conditions defined in the recommendations of the "Groupe Français de Transplantation Fécale" (Sokol et al., 2015), in the article entitled "Practical implementation of faecal transplantation" by Kapel $N_2$. et al., 2014 and in the ANSM recommendations (2015).

In the mixture of cryoprotectants used to preserve the stools in lyophilized form according to the invention, maltodextrin (M) is used with trehalose (T) with an M/T weight ratio ranging from 35/65 to 45/55, and preferably at 40/60.

According to a preferred embodiment of the invention, the cryoprotectants present in the mixture are exclusively maltodextrin and trehalose.

According to another embodiment of the invention, the cryoprotectants present in the mixture include maltodextrin and trehalose, and at least one other cryoprotectant selected among mannitol, sorbitol, fructose, glucose, maltose, sucrose, gelatine, starch, foetal bovine serum and milk.

The invention also relates to a lyophilized composition comprising a microbiota in its ecosystem (MIIE) and a mixture of cryoprotectants, wherein said mixture of cryoprotectants comprises maltodextrin (M) and trehalose (T) used in an M/T weight ratio ranging from 35/65 to 45/55, and preferably with a weight ratio of 40/60.

In the composition according to this invention, maltodextrin is used with trehalose with an M/T weight ratio ranging from 35/65 to 45/55, and preferably with a weight ratio of 40/60.

According to a preferred embodiment of the invention, the cryoprotectants present in the lyophilized composition are exclusively maltodextrin and trehalose.

According to another embodiment of the invention, the cryoprotectants present in the lyophilized composition include maltodextrin and trehalose and at least one other cryoprotectant selected among mannitol, sorbitol, fructose, glucose, maltose, sucrose, gelatine, starch, foetal bovine serum and milk.

The lyophilized composition according to the invention contains a mixture of MIIE and cryoprotectants in a weight content of, respectively, 15 to 35% and 85 to 65% of the lyophilized composition respectively, and preferably in a weight content of 18 to 28% and of 82 to 72%. These weight contents may vary depending on various parameters including the degree of hydration of the sample of MIIE and its lipid content, fibre content and cell debris content, which may vary, particularly in the case of stools. The person skilled in the art will adapt the weight content in order to optimize the composition that undergoes lyophilization.

Thus, the inventors have shown that the lyophilization of a composition comprising stools and a mixture of cryoprotectants, comprising maltodextrin and trehalose, allow to maintain the viability and biodiversity of the faecal microbiota over a prolonged period of at least 6 months. They also demonstrated that the production of bacterial metabolites in the lyophilizate can be maintained. In addition, they have shown the ability of the lyophilizate to inhibit the growth of *Clostridium difficile* in vitro.

The term "viability of the microbiota", according to this invention, relates to the living part of the faecal microbiota.

The "biodiversity of the faecal microbiota" is represented by the different microbial populations in the MIIE. Preservation of its constitutive populations can be assessed by examining the stability of representative groups of microorganisms in the microbiota.

In a preferred embodiment, this invention relates to a lyophilized composition comprising stools and a mixture of cryoprotectants comprising maltodextrin (M) and trehalose (T) with an M/T weight ratio ranging from 35/65 to 45/55, and preferably with a weight ratio of 40/60.

In this preferred embodiment wherein the MIIE consists of stools, the stool weight proportion represents 15 to 35% of the lyophilized composition, and the weight proportion of the mixture of cryoprotectants represents 85 to 65% of the lyophilized composition.

In an even more preferred embodiment wherein the MIIE consists of stools, the stool weight proportion represents 15 to 35% of the lyophilized composition, the weight proportion of the mixture of cryoprotectants represents 85 to 65% of the lyophilized composition, and the mixture of cryoprotectants comprises maltodextrin (M) and trehalose (T) in an M/T weight ratio ranging from 35/65 to 45/55, and preferably in a weight ratio of 40/60.

In addition to maintaining the bacterial load, as well as its viability and its diversity, by preserving the balance between the dominant bacterial groups belonging to the Firmicutes and Bacteroidetes phyla, the composition according to the invention features a significant advantage over bacterial strain mixtures (Allen-Vercoe E. et al., 2013). Indeed, the stool composition according to the invention allow to retain the faecal microbiota in its original natural ecosystem (faecal ecosystem). Interactions between the various components, as well as the functional capabilities of this complex material are thus preserved and the individual receiving the FMT has the same advantages as with the transplantation of fresh stools or the administration of a bacterial filtrate (Ott et al., 2016).

The term "faecal ecosystem" means, according to this invention, everything that constitutes the stool, i.e. not only the bacteria, viruses, fungi and bacteriophages, but also bacterial products secreted or not, including metabolites such as short-chain fatty acids, the bacteriocins, and all other biologically active molecules produced by bacteria or other micro-organisms of the microbiota and intestinal cells that are desquamated or in a state of apoptosis (enterocytes, immune cells of the lamina propria) and their excretion/secretion products (secretory IgA, calprotectin, cytokines and other anti-inflammatory or antimicrobial peptides . . . ), the carbohydrate monosaccharide and polysaccharide elements, such as fibres and cellulose coming from the indigestible portion of plants, protein and lipid residues, trace elements, mucus . . . .

The composition of the invention is particularly well suited for oral administration.

It can, for example, be in the form of a gastro-resistant capsule or tablet, or granules that do not require rehydration or the use of a spray, depending on the treated individual.

According to a particular embodiment of the invention, the lyophilized composition is in the form of a capsule or a gastro-resistant tablet. This presentation is particularly suitable for oral administration in humans. The term "gastro-resistant capsule or tablet" means, according to this invention, an oral galenic and enterosoluble form that is resistant to gastric juices.

Such formulations may also contain a pharmaceutically-acceptable carrier that renders the lyophilized composition suitable for administration to the subject receiving treatment. This carrier is preferably inert, and in any case capable of maintaining the viability and diversity of the microbiota in its ecosystem and releasing the lyophilized composition at the appropriate site.

Thus, this invention also relates to a gastro-resistant capsule comprising the lyophilized composition as described above.

The filling of said capsules, whether performed manually or industrially, is achieved volumetrically. For this purpose, it is necessary that the lyophilizate is pulverized and that the powder to be distributed presents a good fluidity to ensure a regular filling of the capsules (Le Hir et al., 2016).

The flow properties of a powder can be assessed with the test "2.9.16. Flow" of the European Pharmacopoeia (European Pharmacopoeia, 2016), which measures the time required for a test sample to flow through the orifice of a funnel featuring standardized dimensions. A time of 10 seconds or less/100 g of powder is considered as an excellent flow. In contrast, a flow time of a powder that does not flow is graded as "infinite". This is the case of raw faecal lyophilizate, which can therefore not be used in that form to fill capsules.

To overcome this limitation, the inventors have developed capsules comprising the lyophilized composition as described above, supplemented with flow excipients such as flow diluents and lubricants that are able to improve the flow of the faecal lyophilizates.

The flow excipients used in the capsules containing the lyophilizates according to the invention are chosen among inorganic excipients, such as dicalcium phosphate, maltodextrin, talcum, hydrophilic colloidal silica and hydrophobic colloidal silica.

Therefore, according to the invention, the gastro-resistant capsule comprises a lyophilized composition according to definition given above, mixed with at least one flow excipient selected among a flow lubricant and/or a flow diluent for direct compression.

According to a particular embodiment, the flow excipient is a flow lubricant used in the quantities that are generally implemented for this purpose; preferably the amount of lubricant mixed with the lyophilizate ranges from 0.1 to 1% of the weight of the lyophilizate and lubricant mixture, and preferentially the quantity of lubricant is 0.5% of the weight of the lyophilizate and lubricant mixture.

The flow lubricant may be selected among talcum, hydrophobic colloidal silica, or hydrophilic colloidal silica; preferentially, hydrophobic colloidal silica is used.

According to a particular embodiment, the flow excipient is a diluent for direct compression used in quantities that are generally implemented for this purpose; preferably the amount of diluent mixed with the lyophilizate ranges from 10 to 90% of the weight of the lyophilizate and diluent mixture, and preferentially between 15 to 75% or 25 to 50% of the weight of the lyophilizate and diluent mixture.

The diluent for direct compression may be selected from dicalcium phosphate or nebulized maltodextrin.

According to another particular embodiment, the flow excipient comprises a flow lubricant and a diluent for direct compression as defined above and in the stated proportions.

For example, the MIIE lyophilizate and flow excipient mixture is composed of:
- a proportion of hydrophobic colloidal silica of 0.1 to 1%, and preferentially of 0.5% of the weight of the total mixture;
- a proportion of hydrophilic colloidal silica of 0.1 to 1%, and preferentially of 0.5% of the weight of the total mixture and a proportion of dicalcium phosphate of 10 to 90%, and preferentially between 15 and 75%, preferentially 25 and 50% of the weight of the total mixture;
- a proportion of talcum of 0.1 to 1%, and preferentially of 0.5% of the weight of the total mixture and a proportion of nebulized maltodextrin of 10 to 90%, and preferentially between 15 and 75% of the weight of the total mixture.

In this context, the development of gastro-resistant capsules prepared from a lyophilized composition is a significant progress in terms of the organoleptic properties of the preparation, of the availability of the transplantation material, of the preservation of the preparation and of the comfort of the person receiving the treatment.

Lyophilization allows to remove the water present in the stool. Indeed, normal stools generally contain a water proportion of between 75 and 85%. After lyophilization, a 50 g stool corresponds to approximately 7.5-12.5 g of lyophilized microbiota, to which is added the mixture of cryoprotectants.

Compared with conventional methods relating to the administration of stools, whether fresh or frozen stools, the administration in a lyophilizate form that can be included in gastro-resistant capsules therefore promotes standardised preparation methods and improves the acceptability by the person receiving treatment. Thus, when oral administration in the form of a lyophilizate is well established in medical practice, morbidity rates can be lowered and the cost of the faecal transplantation can be reduced. Indeed, the oral administration of the FMT as a lyophilized preparation will no longer be associated with technical processes that require specialised personnel and needing day hospitalisation, as is currently the case for administration by nasoduodenal, colonoscopy or rectal of preparations from fresh or frozen stools. Compared with the administration of frozen capsules, administration in the form of a lyophilizate will facilitate the manufacturing and storage process, thereby improving the standardisation of the preparation. Furthermore, the use of lyophilized formulations will improve accessibility to FMT equipment, which is a crucial point when responding to emergency situations that may be encountered, for example, in the context of recurrent *Clostridium difficile* infections.

Therefore, this invention also relates to a method of preserving stools by lyophilization and involving the use of mixtures of cryoprotectants as defined above. This method allows for the preservation lyophilized stools for at least 3 months and for a period of up to 7 months and even beyond, by ensuring the continued viability and diversity of the microbiota as described above.

Lyophilized stools that have been preserved according to the invention can be administered as part of an allogeneic or autologous FMT. Indeed, FMT can consist in the transfer of stools between two individuals of the same species, or in the administration to a same individual, who was initially a healthy donor at a given moment, and who become a person receiving the treatment at a later date. Thus, a healthy individual may subsequently use the lyophilized composition comprising a stool preparation made from his/her donation, at the moment he/she needs it.

Another purpose of this invention relates to a lyophilized composition or a gastro-resistant capsule as described above, for its use as a medicament.

This invention therefore relates to the lyophilized composition or the gastro-resistant capsule described above for its use in the treatment of a disease or a disorder related to an imbalance of the intestinal microbiota.

Indeed, the intestinal microbiota is a balanced ecosystem that is continuously regulating itself. Various attacks threaten to break this balance. Dysbiosis is a loss of diversity or an imbalance of the microbiota resulting from an excess of harmful micro-organisms and/or the relative insufficiency of micro-organisms that are beneficial to the host. Therefore, the indicated use of the lyophilized composition according to the invention is the same as that associated with dysbiosis. As such, the terms "diseases or disorders related to an imbalance of the intestinal microbiota" are taken to include *Clostridium difficile* colitis and its recurrence, chronic inflammatory bowel diseases such as Crohn's disease and ulcerative colitis, irritable bowel syndrome, the presence of multidrug-resistant bacteria, constipation, traveller's diarrhoea, gastrointestinal infections, autoimmune diseases, diverticulosis, type 1 and type 2 diabetes, metabolic syndrome, obesity, rheumatoid arthritis, ankylosing spondylitis and sacroiliitis, chronic fatigue syndrome, halitosis, allergy, acne, insomnia, depression and neuropsychiatric diseases such as, for example, Parkinson's disease and autism spectrum diseases.

In a preferred implementation, the lyophilized composition according to the invention is used in the treatment of *Clostridium difficile* colitis. In this context, the presence of bacterial metabolites preserved in lyophilized products can have a major beneficial effect in the fight against *C. difficile*.

The lyophilized composition may also be used in the treatment of inflammatory bowel disease, multidrug-resistant bacteria, type 1 and type 2 diabetes, metabolic syndrome, obesity and autism spectrum diseases.

The preservation of the environment associated with the microbiota can significantly contribute to the therapeutic effect of the FMT.

The lyophilized composition or gastro-resistant capsule according to the invention may also be used as a relay for an oral antibiotic treatment, such as metronidazole or vancomycin (first-line therapy used to treat *Clostridium difficile* infections), particularly for the treatment of recurring *Clostridium difficile* colitis, where subjects have become insensitive to repeated antibiotic treatment.

A composition of lyophilized MIIE according to the invention is designed to be administered to a humans or animals.

In a context where action plans involving antibiotherapy to limit the risk of development of multidrug-resistant bacteria are on the rise, the use of such a lyophilized composition provides an alternative in veterinary medicine, and in particular in organic farming. Thus, the lyophilized composition according to the invention can be used in humans but also in animals such as pigs, cattle, sheep, rodents, lagomorphs, carnivores, equines, birds, reptiles, and especially in pig, cattle, chicken, rat, rabbit, dog, cat, and horse. FMT is a method that has been empirically used for many years and that has undergone significant development in veterinary medicine, and its administration in the form of lyophilized stools will clearly facilitate its implementation.

For the purpose of facilitating its administration to animals, a lyophilized composition of MIIE may be prepared in the form of granules that require neither rehydration nor spraying. The person skilled in the art will adapt the galenic form so as to render it as suitable as possible, depending on the animal undergoing treatment.

Another purpose of this invention relates to a method for preparing a lyophilized composition of MIIE according to the invention, and comprising the following steps:
  collection of the MIIE, and stools in particular;
  dilution of the MIIE with a mixture of cryoprotectants as described above, with an M/T weight ratio ranging from 35/65 to 45/55, and with a preferred M/T weight ratio of 40/60;
  lyophilization of the mixture achieved in the previous step and obtaining the lyophilized composition.

According to a particular embodiment, lyophilization can be conducted by applying a freezing temperature ranging from −20° C. to −80° C., over a period of several tens of minutes to several hours. In a preferred embodiment, the freezing step is carried out at −80° C. for 30 min. The person skilled in the art will adapt these conditions.

As mentioned above, the MIIE and mixture of cryoprotectants is such that it comprises a weight proportion of 15-35% of MIIE, and a weight proportion of 85-65% of cryoprotectants out of the total weight of the lyophilized composition, and a preferred weight content ranging from 18 to 28% and from 82 to 72%. These weight contents may vary depending on various parameters including the degree of hydration of the sample of MIIE and its lipid content, fibre content and cell debris content, which may vary, particularly in the case of stools. The person skilled in the art will adapt the weight content in order to optimize the composition that undergoes lyophilization.

In a particular embodiment, this invention relates to a process for preparing a gastro-resistant capsule comprising a lyophilized composition according to the invention, and comprising the following steps:
  preparation of a lyophilized composition;
  lyophilizate spray into powder form;
  optionally addition of one or more excipients improving the flow of the lyophilizate;
  filling the envelope of the gastro-resistant capsule with said lyophilized mixture;
  sealing the capsules.

Particular embodiments are described in the following examples. Their only purpose is to illustrate the invention and to make it easier to understand, and they are in no way limited thereto.

EXAMPLE 1

1. Materials and Methods
1.1. Faecal Sampling

The selection of lyophilization conditions is based on the study of 3 stools provided by healthy independent volunteers and placed immediately after emission in the presence of a GENbagAnaer® system installed in the sample pot for incubation. The sample was sent straight to the laboratory after emission, within less than 1 hour. A fraction of each stool is preserved with GENbagAnaer® as a control for immediate analysis.

1.2. Choice of Cryoprotectants
The cryoprotectants used for this study are:
glycerol at 10% (G)
reconstituted skimmed and pasteurized milk powder at 10% (L).
maltodextrin, at a concentration of 5% (M).
trehalose, at a concentration of 5% (T5) and 10% (T10).

mixture of maltodextrin at a concentration of 6.7% and trehalose at a concentration of 10%, or in an M/T weight ratio of 40/60 (MT).

NaCl solution at a concentration of 9% as a control, as it is generally used to dilute fresh faecal matter.

Each solution was packaged in sterile pots and stored at +4° C. until use.

1.3. Preparation of the Faecal Lyophilizate

The stools were diluted 10 times in the cryoprotectant solution and homogenized using an Ultraturrax®-type homogenizer fitted with a disposable stem. The suspended solutions were placed in lyophilization vials, with a volume corresponding to 3 ml for 300 mg of the native stool sample.

For each condition tested, and for each of the 3 analysed stools, a suspension vial was immediately placed in the presence of a GENbagAnaer® system to assess the effect of different cryoprotectants on the viability of the bacteria in the microbiota of each diluted and non-lyophilized stool.

The remaining vials are immediately placed at −80° C. After freezing for 30 minutes, the vials are placed in the lyophilizer (FreeZone®, 6 Liter, Freeze Dry System, Model 77530, Labcono Corporation, Kansas City, Mo., USA), in which the trap has already cooled for a 24-hour period under automatic cycle. At the end of this period of lyophilization, the vials are sealed under vacuum and secured with aluminium tops.

For each stool and each condition of cryo-preservation, a series of vials is sent to a microbiology laboratory for analysis of the microbiota and 2 series are stored at 4° C. for stability studies for 3-4 months and 7-8 months.

1.4. In Vitro Studies of the Viability of the Microbiota Depending on Lyophilization Conditions The first step of the microbiological study was the analysis of non-lyophilized diluted stools to test the effect of the dilution in the presence of the different cryoprotectants on maintaining the diversity of the microbiota and its viability. For this purpose, a certain amount of the dilutions made with 10% milk (L), 10% glycerol (G), 5% maltodextrin (M), 5% trehalose (T) 10% trehalose (T10) and a mixture of 6.7% maltodextrin and 10% trehalose, i.e. an M/T weight ratio of 40/60 (MT) were immediately placed, after the preparation of the faecal lyophilizate, under anaerobiosis and microbial cultures were made immediately.

The second step of the process related to the study of lyophilizates. Analyses were conducted during the week after the preparation, and then after 3-4 months and 7-8 months of storage at 4° C. Each lyophilizate is reconstituted with 3 ml of sterile peptone water, which corresponds to the volume of diluted stool initially present in each vial.

For the analysis of strictly aerobic and anaerobic microbiota, the non-lyophilized stools and the reconstituted lyophilizates were diluted 10 to 10 and seeded on selective and non-selective media (Rougé et al., 2010). The media incubated aerobically and in an anaerobic unit ($N_2/CO_2/H_2$:80/10/10) at 37° C. are shown in Table 1.

TABLE 1

The media used for the analysis of the microbiota for each culture

| Searched elements of the microbiota | Agar base | Incubation/ reading |
| --- | --- | --- |
| Total anaerobic population | Colombia + cysteine (Cc) + blood + neomycine (100 mg/ml) | 37° C. Anaerobic unit Reading and |
| Bacteroides sp., Prevotella sp. | Cc + Blood + Kanamycine (100 mg/ml) + vancomycine (7 mg/ml) | counting at 48 hours and 5 days |
| Clostridium difficile | CC + blood + Clostridium difficile medium (CLO-M Biomérieux) | |
| Other Clostridium | CC + mupirocine (100 mg/ml) + full milk (5 ml) + neutral red (40 mg/ml) | |
| Bifidobacterium sp. | WCB (Wilking-Chalgren for Bifidobacteria) + mupirocine (100 mg/ml) | |
| Lactobacillus sp. | MRS (Nan, Rogosa, Sharpe agar) | |
| Total aerobic population | Trypticase soy | 37° C. Aerobiosis |
| Enterobacteria | Drigalski | Reading at 24 hours |
| Enterococcus sp. | Enterococcosel | |
| Staphylococcus sp. | Chapman 110 | |
| Yeast | Sabouraud Chloramphenicol | |

The quantification of bacteria extremely oxygen sensitive (EOS), such as bacteria of the *Clostridium leptum* group was conducted out by differential culture in the presence or absence of oxygen. For this purpose, fresh stool samples (TO) and the various lyophilized samples rehydrated in peptone water were successively diluted in a very rich no selective culture medium (YBHI corresponding to a brain-heart medium enriched with yeast extract supplemented with cellobiose, maltose and cysteine). This medium was developed to allow the culture of bacteria extremely difficult to cultivate bacteria, such as the *Faecalibacterium prausnitzii*. Once the ad hoc dilutions in strict anaerobic conditions were completed, their ability to resist or not to the presence of oxygen was assessed by parallel cultures in 2 dishes, one of which was subjected to an aerobic atmosphere for 60 minutes while the other was not. This method allows to evaluate the percentage of strictly viable anaerobic bacteria in different samples at different times after lyophilization.

2. Results 2.1. Effect of Different Cryoprotectants on the Diversity and Viability of the Microbiota Before Lyophilization.

Figure 1:
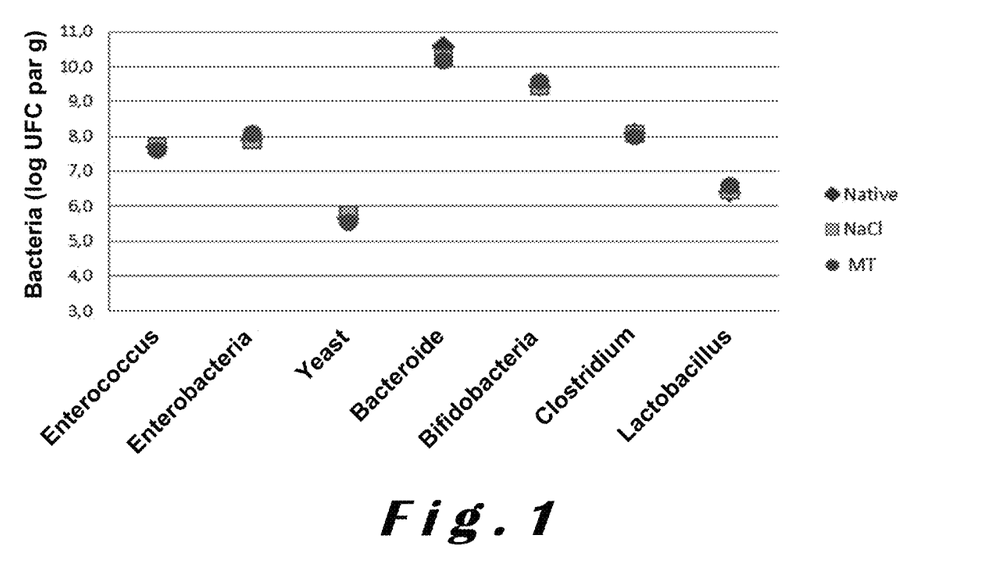
FIG. 1: Representation of major bacterial groups and yeasts recovered after growth in native stools and diluted in NaCl 9% or within the maltodextrin cryoprotectant mixture comprising 6.7% maltodextrine and 10% trehalose (MT). The results shown in FIG. 1 correspond to those obtained for stool 3.

A stool dilution in the various assessed cryoprotectants, and in particular in the MT mixture, had no significant impact on bacterial load, and didn't influence the equilibrium of the different main genera of cultivable microbiota, compared with the native stool or the stool diluted in 9% NaCl (which corresponds to the preparation used for FMT with fresh stools) (FIG. 1). The major groups of the microbiota remain viable.

2.2. Effect of Lyophilization on the Viability of the Microbiota Based on the Cryoprotectants Used The total bacterial load was assessed during the week following lyophilization, or at MO. The results are presented in FIG. 2.

The three cryoprotectants tested, namely a 5% trehalose solution (T5), a 10% trehalose solution (T10) and a mixture of 6.7% maltodextrin and 10% trehalose (TM), allow to provide a stability greater than 90% of the total bacterial load of cultivatable bacteria during lyophilization; this result corresponds to a loss of about 1 log compared with the existing load in a native stool, or a stool diluted in 9% NaCl before lyophilization.

The total bacterial load measured up to 7 months post-lyophilization has not change much (FIG. 3).

Furthermore, these three cryoprotectants allow efficient preservation of EOS bacteria during lyophilization (FIG. 4).

2.3. Effect of Lyophilization on the Diversity of the Microbiota Depending on the Different Cryoprotectants Used Among the three cryoprotectants tested above, the cryoprotectant mixture of 6.7% maltodextrin and 10% trehalose (or in a weight ratio of 40/60) is the one that gives the best results maintaining the main genera constituting the faecal microbiota alive, despite a decrease in certain strict anaerobic genera of about 1 to 2 log, for stool 3 (FIG. 5) (and up to 4 log for other stools—not shown). Conversely, the 10% glycerol solution is not very protective both for aerobic genera and anaerobic genera (result not shown).

Strictly anaerobic genera (*Clostridium* sp. and *Bacteroides* sp.) remain dominant when the study is conducted within one week after lyophilization (FIG. 6). Preservation at 4° C. of the lyophilizate has little impact, and shows an additional loss of around 1.5 log for *Bacteroides* sp. after 3 months of storage at 4° C. and a loss of 1 log at 8 months for *Clostridium* sp. (FIG. 6). In any case, the dominant genera of the microbiota remain dominant during the preservation.

The results obtained with stool 2, rich in *Bifidobacterium* sp. showed the stability of that group, for up to 6 months post-lyophilization in the MT mixture (result not shown).

Taken together, these results show that the MT mixture is the one that allows the best preservation of lyophilized faecal microbiota, both in terms of viability and of diversity and for a period of up to 6 months after lyophilization.

EXAMPLE 2

1. Materials and Methods

Pursuant to the method described in example 1, three additional faecal samples identified as S4, S5 and S6 were diluted in the presence of a cryoprotectant mixture of 6.7% maltodextrin and 10% trehalose (or in an M/T weight ratio of 40/60) and then lyophilized.

2. Results 2.1. Stability of the Bacterial Ecosystem in Lyophilizates After 6 Months of Storage 2.1.1. Analysis of the Bacterial Viability and Diversity in Lyophilizates After 6 Months of Storage The strictly anaerobic population was analysed based on the count of representative bacteria groups: *Bifidobacterium* spp. and *Bacteroides* spp.

Regarding the *Bifidobacterium* spp. genus, it remains an integral part of the dominant microbiota and no significant changes during the 6-month preservation period.

For the *Bacteroides* spp., genus, there were inter-individual variations resulting in a loss of about 1.5 to 4 log over a 6 month-period.

The optional aerobic-anaerobic populations from the different samples were analysed based on the count of bacterial groups *Lactobacillus* spp., *Enterococcus* spp. and *Enterobacteriaceae*. The stability and viability of these genera and bacterial groups post lyophilization throughout the 6-month preservation period are confirmed.

These results show that the lyophilization process mostly retains the viability of the various target bacterial populations without inducing changes in the overall balance between the major bacterial groups, and that preservation remains stable over a 6-month preservation period (FIG. 7).

2.1.2. Study of Bacteria Extremely Oxygen Sensitive

One of the specific features of faecal microbiota is the presence of bacteria extremely oxygen sensitive (EOS) that can be affected by the lyophilization process.

These EOS bacteria are detected both for the native stool and in faecal lyophilizates in all analysed samples (FIG. 8). When these EOS bacteria are expressed as a percentage relative to the total quantity of anaerobic bacteria (CFU/ml), the level remains stable throughout the preservation period (3 to 6 months depending on the sample) and the quantity of strictly anaerobic bacteria is not affected by the preservation process. These results show that the lyophilization does not affect bacterial populations that show extreme oxygen sensitivity.

2.2. Stability of the Functions of Bacterial Ecosystem in the Lyophilizates 2.2.1. Detection of Metabolites in the Lyophilizates The production of bacterial metabolites, i.e. short-chain fatty acids, was assessed in the 72 h lyophilizate compared with the native stool. Out of 3 analysed samples, lyophilization induces preservation of fermentation products with the concentration of short-chain fatty acids increased 2 to 4 fold for acetate and propionate, depending on the stool samples, and 2 to 6 fold for butyrate. Bacterial metabolites, although volatile, are present in the lyophilizates. The increase of their concentration would be a consequence of lyophilization that causes a concentration of the metabolites (FIG. 9).

2.2.2. Detection of the Anti-*Clostridium difficile* Effect in the Lyophilizates The anti-*Clostridium difficile* effect in native stools and in lyophilizates was analysed in vitro in the presence of two strains of *Clostridium difficile*, including one toxinogen strain (strain 630) and one non-toxinogen strain (strain PCD1). When the growth of the strains is inhibited, a pale circle appears around the inoculation area: this is the inoculation circle.

Various controls, known for their anti-*Clostridium difficile* effects, were systematically used as positive controls. Acetic acid (AA) as well as lactic acid (AL) was therefore used at different concentrations (300, 400, 500 mM). In each dish, an inhibition circle was observed in the presence of acetic acid and/or lactic acid.

Pure strains were used as control, i.e. a *Lactobacillus* strain and a *Bifidobacterium* (CB) strain, which do not cause inhibition circles to appear.

In the presence of native stools (S or NS) and in the presence of stools that were frozen at −80° C. for 72 hours (T1, T2, and T3), no inhibition circle is visible whereas an inhibition circle is visible in the presence of lyophilizates (FIG. 10).

The results of these various experiments reveal the presence of an inhibition area for acetic acid and lactic acid, and for the lyophilizates of all of the analysed stools. The inhibitory capacity of in vitro development of *C. difficile* by a stool is therefore potentiated by lyophilization.

All the results shown in example 2 confirm the stability and viability of the microbiota in the lyophilizate over a period of at least 6 months and that the functional capacities of the bacteria are maintained within the lyophilizate, in particular with the preservation of bacterial metabolites of interest and an anti-*Clostridium difficile* effect in an in vitro study model.

EXAMPLE 3

1. Materials and Methods
1.1. Stool Lyophilizates

Four stools from healthy donors were processed with the method described in example 1 for the purpose of obtaining four faecal lyophilizates: S4, S5, S6 and S7, where S7 representing an additional faecal sample compared with example 2.

1.2. Choice of the Excipients
Diluents

The selection of diluents is based on their inert nature and, in particular, on the absence of specific intestinal effects.

The selected diluents are a mineral excipient, dicalcic phosphate (Anhydrous Encompress®, JRS Pharma, Rosenberg, Germany) and nebulized maltodextrins (Emdex®, JRS Pharma Rosenberg Germany) where the latter type of excipient is already in the composition of the lyophilizate. The density and the flow time of these both pure excipients are respectively of 0.79 g/mL and 3 seconds 18/100 g for anhydrous Encompress®, and 0.68 g/mL and 6 seconds 03/100 g for Emdex®.

Lubricants

Three flow lubricants were selected: talcum (Cooper, France), hydrophilic colloidal silica (Aérosil® 200 Pharma, Kraemer & Martin GmbH, St-Augustin, Germany), and a hydrophobic colloidal silica (Aérosil®, R972, Degussa-Hüls, Courbevoie, France).

1.3. Measuring the Flow Time and Mixing the Lyophilizates to the Excipients This test was conducted according to monograph 2.9.16 of the European Pharmacopoeia, first on the lyophilizates alone, and then after inclusion of a flow lubricant used at 0.5% and, when necessary, of a diluent tested in the 75/25, 50/50 and 25/75 weight ratio. These mixtures were achieved manually.

The density of the final mixtures featuring a good fluidity was measured for all the mixtures, before being reported by calculation to 1 mL.

1.4. Making Capsules with the Mixtures Featuring a Good Flow.

N°100 capsules associated with a significant volume of 0.95 mL and of a size compatible xith relatively easy ingestion (23.3 mm) in length) were selected. They were filled manually with a capsule filler and mixtures featuring a good flow.

2. Results
2.1. Study of the Flow Characteristics and the Density of the Lyophilizates Table 1 shows the results of the tests conducted on the lyophilizates

TABLE 1

Flow of raw faecal lyophilizates, and with mixtures containing a flow lubricant and/or diluent, and density of the final volumes.

| | TESTED MIXTURES | WEIGHT RATIO | FLOW (AVERAGE OUT OF 3 MEASUREMENTS FOR X G) | DENSITY |
|---|---|---|---|---|
| S4 | Raw faecal lyophilizate | | Infinite | Not determined |
| | Faecal lyophilizate/talcum | 99.5/0.5 | Infinite | |
| | Faecal lyophilizate-talcum*/Emdex ® | 75/25 | Infinite | |
| | | 50/50 | 4s16 (taps) | |
| | | 25/75 | 0s69 for 13.70 g (0s69/0s68/0s71) | 13.70 g/26 mL (0.53 g/mL) |
| S5 | Raw faecal lyophilizate | — | Infinite | Not determined |
| | Faecal lyophilizate/Aérosil ® 200 | 99.5/0.5 | Infinite | |
| | Faecal lyophilizate/Aérosil ® 200*/Anhydrous Emcompress ® | 75/25 | 0s84/0s37/Infinite (taps) | |
| | | 50/50 | 0s53/0s31/Infinite | |
| | | 25/75 | 0s57 for 10.86 g (0s56/0s48/0s68) | 10.86 g/17 mL (0.64 g/mL) |
| S6 | Raw faecal lyophilizate | — | Infinite | Not determined |
| | Faecal lyophilizate/Aérosil ® R927 | 99.5/0.5 | 0s30 fir 1.466 g (0s35/0s25/0s31) | 1.466 g/4.5 mL (0.33 g/mL) |
| S7 | Raw faecal lyophilizate | — | Infinite | Not determined |
| | Lyophilizate/Aérosil ® R927 | 99.5/0.5 | 0s26 for 3.296 g (0s25/0s25/0s27) | 3.296 g/7 mL (0.47 g/mL) |

*at a weight ratio of 99.5/0.5

None of the tested raw faecal lyophilizates tested alone has any flow properties. It is therefore impossible to put them in capsules as they are.

Despite their role of flow lubricants, talcum and Aérosil® 200 used at 0.5% did not allow to improve the fluidity of the lyophilizates (S5 and S5).

The Emdex® and anhydrous Emcompress® diluents are efficient in improving the flow. The improvement occurs with the ratio 50/50 for the lyophilizate S4-talcum/Emdex® mixtures, and with the ratio 75/25 for the lyophilizate S5-Aérosil® 200/anhydrous Emcompress® mixture. At a ratio of 25/75 between the lyophilizate and the diluent, the mixture becomes fluid with a flow time of 0s69 for 13.70 g (S4) and 0s57 for 10.86 g (S5).

Finally, the Aérosil® R972 flow lubricant used alone at 0.5% has led to a significantly improvement of the fluidity of the lyophilizates S6 (0s30 for 1.466 g) and S7 (0s26 for 3.296 g).

The density of the mixtures ranges from 0.53 to 0.64 g/mL for "lyophilizate/flow lubricant/diluent" mixtures and from 0.33 to 0.47 g/mL for the "lyophilizate/flow lubricant" mixtures.

2.2. Making Capsules of the Mixtures

Table 2 shows the number of prepared capsules for each sample, and the mass of the lyophilizate integrated in each capsule. The theoretical mass of fresh matter initially implemented is reported in the last column.

TABLE 2

Characteristics of capsules prepared with lyophilized samples.

| | NUMBER OF PREPARED CAPSULES | MIXTURE MASS/CAPSULE | LYOPHILIZATE MASS/CAPSULE | THEORETICAL MASS OF FRESH MATTER IN n CAPSULES |
|---|---|---|---|---|
| S4 - talcum/Emdex ® | 20 | 500 mg | 125 mg | 1754 mg |
| S5 - Aérosil ® 200/Anhydrous Emcompress ® | 18 | 603 mg | 151 mg | 3000 mg |
| S6 - Aérosil ® R972 | 5 | 293 mg | 293 mg | 1792 mg |
| S7 - Aérosil ® R972 | 7 | 471 mg | 471 mg | 5000 mg |

The case of samples S6 and S7 is the most favourable since the dilution of the lyophilizate is insignificant, because only 0.5% flow lubricant was added. However, there is a rather important variability observed between two samples that, with the same volume, can represent 293 mg (S6) or 471 mg (S7) of dry matter. This stems from the density difference between the two samples.

With regard to samples S4 and S5, the dilution of the lyophilizate is more important because of the adding of 75% diluent, in addition to the 0.5% of flow lubricant. With the same volume, the mass of the lyophilizate varies from 125 mg (S4) to 151 mg (S5) of dry matter, with respect to the density of each sample.

This study shows that powdered faecal microbiota lyophilizates do not have a fluidity property and therefore can not be put into capsules alone.

However, it is possible to improve the flow properties of the lyophilizates by mixing, either with 75% diluent (Emdex® maltodextrins, anhydrous dicalcic phosphate, anhydrous Emcompress®) or with 0.5% of flow lubricant (hydrophobic colloidal silica, Aérosil® R972).

BIBLIOGRAPHY

Allen-Vercoe E, Petrof E O. Artificial stool transplantation: progress towards a safer, more effective and acceptable alternative. Expert Rev Gastroenterol Hepatol 2013; 7:291-3.

ANSM. Rapport. La transplantation de microbiote fécal et son encadrement dans les essais cliniques, Mars 2014, mise à jour juin 2015.

Béal C and Fonseca F. Freezing of probiotic bacteria. P. 179-212. Advances in probiotic technology. Eds Foerst P. and Sativarangkna C. 2015, CRC Press, Boca Raton, USA.

Borody T, Fischer M, Mitchell S, Campbell J. Fecal microbiota transplantation in gastrointestinal disease: 2015 update and the road ahead. Expert Rev Gastroenterol Hepatol. 2015; 9:1379-91. Carvalho A. S., Silva J., Ho P., Texeira P., Malcata F. X. and Gibbs P. Relevant factors for the préparation of freeze-dried lactic acid bacteria. Int. Dairy J 2004, 14: 835-47.

Debast S B, Bauer M P, Kuijper E D. European Society of Clinical Microbiology and Infectious Diseases: update of the treatment guidance document for Clostridium difficile infection. Clin Microbiol Infect 2014; 20 Suppl 2:1-26.

Hamilton M J, Weingarden A R, Sadowsky M J, Khoruts A. Standardized frozen preparation for transplantation of fecal microbiota for recurrent Clostridium difficile infection. Am J Gastroenterol 2012; 107:761-7.

Kapel N, Thomas M, Corcos O, Mayeur C, Barbot-Trystram L, Bouhnik Y, Joly F. Practical implementation of faecal transplantation. Clinical Microbiology and Infection 2014; 20:1098-105.

Kelly C R, Kahn S, Kashyap P, Laine L, Rubin D, Atreja A, Moore T, Wu G. Gastroenterology. 2015 July; 149(1): 223-37.

Le Hir A, Chaumeil J C, Brossard O, Charrueau C, Crauste-Mander S. Pharmacie galénique, bonnes pratiques de fabrication des médicaments. Elsevier Masson S A S, Issy-les-Moulineaux, France, $10^{4mi}$ édition, 2016.

Lee C H, Steiner T, Petrof E O, Smleja M, Roscoe D, Nematallah A, Weese J S, Collins S, Moayyedi P, Crowther M, Ropeleski M J, Jayaratne P, Higgins D, LI Y, Rau N V, Kim P T. Frozen vs Fresh Fecal Microbiota Transplantation and Clinical Resolution of Diarrhea in Patients With Recurrent Clostridium difficile infection: A Randomized Clinical Trial. JAMA. 2016; 315:142-149

Ott S J, Waetzig 6H, Rehman A, Moltzau-Anderson J, Bharti R, Grasis J A, Cassidy L, Tholey A, Fickenscher H, Seegert D, Rosenstiel P, Schreiber S. Efficacy of Stérile Fecal Filtrate Transfer for Treating Patients With Clostridium difficile Infection. Gastroenterology. 2016 Nov. 17. pii: S0016-5085(16)35354-9. doi: 10.1053/j.gastro.2016.11.010.

Pharmacopée européenne $8^{inv}$ édition, 2016. Monographie 2.9.16. Ecoulement. EDQM Européen Directory for the Quality of Medicines and Healthcare. https://www.edqm.eu/fr/Pharmacopee-europeenne-8eme-Edition-1563.html Rougé C, Goldenberg O, Ferraris L, Berger B, Rochat F, Legrand A, Göbel U B, Vodovar M, Voyer M, Rozé J C, Darmaun D, Piloquet H, Butel M I, De La Cochetière M F. Investigation of the intetinal microbiota in preterm infants using different methods. Anaerobe 2010; 16:362-370.

Sokol H, Galpertne T, Kapel N, Bourlioux P, Seksik P, Barbut F, Scanzi J, Chast F, Batista R, Joly F, Joly A C, Collignon A, Guery B, Beaugerie L, pour le GroupeFrançais de Transplantation Fécale (GFTF). Transplantation de microbiote fécal dans le cadre des infections à *Clostridium difficile* récidivantes: recommandations pour la pratique clinique courante. Hepato Castro 201; 22:278-90.

Surawicz C M, Brandt U, Binion D G, et ai. Guidelines for diagnosis, treatment, and prévention of *Clostridium difficile* infections. Am J Gastroenterol 2013; 108:478-98.

Van Nood E, Vrieze A, Nieuwdorp M, Fuentes S, Zoetendal E G, de Vos W M, Visser C E, Kuijper E I, Bartelsman J F, Tijssen J G, Speelman P, Dijkgraaf M G, Keller J. Duodenal infusion of donor feces for recurrent *Clostridium difficile*. N Engl J Med 2013; 368:407-15.

Vrieze A, de Groot P F, Kootte R S, Knaapen M, van Nood E, Nieuwdorp M. Fecal transplant: a safe and sustainable clinical therapy for restoring intestinal microbial balance in human disease. Best Pract Res Clin Gastroenterol 2013; 27:127-37.

Youngster I, Sauk J, Pindar C, Wilson R G, Kaplan J L, Smith M B, Alm E J, Gevers D, Russell G H, Hohmann E L. Fecal microbiota transplant for relapsing *Clostridium difficile* infection using a frozen inoculum from unrelated donors: a randomized, open-label, controlled pilot study. Clin Infect Ois 2014a; 58:1515-22

Youngster I, Russell G H, Ziv-Baran T, SaukJi, Hohmann E L. Oral, capsulized, frozen fecal microbiota transplantation for relapsing *Clostridium difficile* infection JAMA. 2014b; 312:1772-8.

Youngster I, Mahabamunuge J, Systrom H K, Sauk J, Khalili H, Levin J, Kaplan J L, Hohmann E L. Oral, frozen fecal microbiota transplant (FMT) capsules for recurrent *Clostridium difficile* infection. BMC Med. 2016 Sep. 9; 14(1): 134. doI: 10.1186/sI2916 016-0680-9.

The invention claimed is:

1. A lyophilized composition comprising a collected microbiota and a mixture of cryoprotectants,
    wherein said mixture of cryoprotectants comprises maltodextrin and trehalose in a maltodextrin/trehalose (M/T) weight ratio ranging from 35/65 to 45/55,
    wherein said microbiota is faecal microbiota contained in stool, and
    wherein said lyophilized composition comprises at least one viable bacterial population that show extreme oxygen sensitivity (EOS) after at least 6 months of storage and wherein said microbiota is unchanged compared with the microbiota existing naturally in the body and further comprises at least bacterial metabolites.

2. The lyophilized composition according to claim 1 in which:
    (i) the collected microbiota is faecal microbiota contained in stool,
    (ii) the stool weight proportion represents 15 to 35% of the lyophilized composition and the weight proportion of the mixture of cryoprotectants represents 85 to 65% of the lyophilized composition, and
    (iii) maltodextrin (M) and trehalose (T) are in a maltodextrin/trehalose (M/T) weight ratio of 40/60.

3. A gastro-resistant capsule comprising a lyophilized composition as defined in claim 1.

4. A gastro-resistant capsule according to claim 3, wherein said lyophilized composition is mixed with at least one flow excipient.

5. A method of treatment of a disease or a disorder related to an imbalance of the intestinal microbiota, comprising administering the lyophilized composition according to claim 1 to a subject in need thereof.

6. The method according to claim 5, wherein the lyophilized composition is administered as a relay for an oral antibiotic treatment, and wherein the subject has recurrent *Clostridium difficile* infections.

7. A method for the preparation of a gastro-resistant capsule of claim 3 comprising the following steps:
    a. collecting the microbiota;
    b. diluting said microbiota with a mixture of cryoprotectants comprising maltodextrin and trehalose in an M/T weight ratio ranging from 35/65 to 45/65;
    c. lyophilizing the mixture achieved in step b to produce a lyophilizate;
    d. pulverizing the lyophilizate obtained in step c into powder form;
    e. optionally adding of one or more excipients improving the flow of the lyophilizate;
    f. filling the envelope of the gastro-resistant capsule with said lyophilized mixture; and
    g. sealing the capsules.

8. The method according to claim 7, wherein said microbiota is faecal microbiota contained in stool and the mixture of cryoprotectants consists of the mixture of maltodextrin (M) and trehalose (T) with an M/T weight ratio of 40/60.

9. A method of treatment of a disease or a disorder related to an imbalance of the intestinal microbiota, comprising administering the gastro-resistant capsule according to claim 3 to a subject in need thereof.

10. The method according to claim 9, wherein the gastro-resistant capsule is administered as a relay for an oral antibiotic treatment, and wherein the subject has recurrent *Clostridium difficile* infections.

11. A method for preserving a microbiota in a lyophilized form, comprising:
    contacting the microbiota with a mixture of cryoprotectants, wherein said mixture of cryoprotectants comprises maltodextrin (M) and trehalose (T) in an M/T weight ratio ranging between 35/65 and 45/55; and
    lyophilizing the microbiota wherein the microbiota is faecal microbiota contained in stool.

* * * * *